United States Patent [19]

Falk

[11] 4,326,426
[45] Apr. 27, 1982

[54] MOLDED SAND INSULATED SAMPLER

[76] Inventor: Richard A. Falk, 519 Westminster Dr., Waukesha, Wis. 53186

[21] Appl. No.: 149,378

[22] Filed: May 13, 1980

[51] Int. Cl.³ .............................................. G01N 1/12
[52] U.S. Cl. ................................................ 73/864.59
[58] Field of Search ................... 73/425.4 R, DIG. 9, 73/864.53, 864.55, 864.59, 864.56

[56] References Cited

U.S. PATENT DOCUMENTS

| | | | |
|---|---|---|---|
| 3,455,164 | 7/1969 | Boyle | 73/864.59 X |
| 4,197,745 | 4/1980 | Kumbrandt | 73/425.4 R |
| 4,206,652 | 6/1980 | Kumbrant | 73/425.4 R |
| 4,250,754 | 2/1981 | Collins | 73/425.4 R |

*Primary Examiner*—S. Clement Swisher
*Attorney, Agent, or Firm*—Henry C. Fuller

[57] ABSTRACT

A molten metal sampler which employs a jacket of sand-sodium silicate mix around the metal mold halves to prevent molten metal splash on the exterior of the mold halves, prevent leakage of molten metal from the mold halves and provide good venting. The sand is molded around the mold halves and, in one embodiment, the protective cardboard sleeve used for connecting the sampler to a manipulating rod serves as the mold for the sand-cement mix.

2 Claims, 4 Drawing Figures

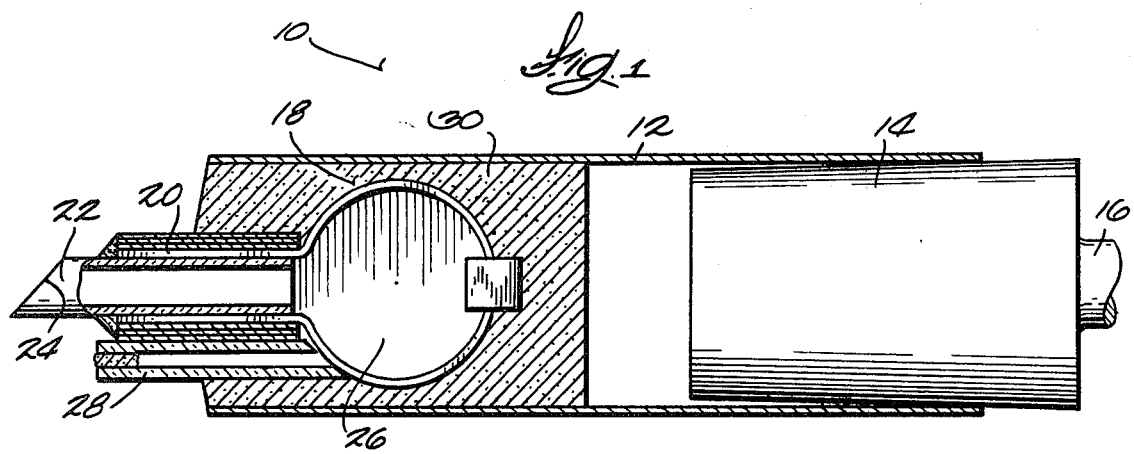
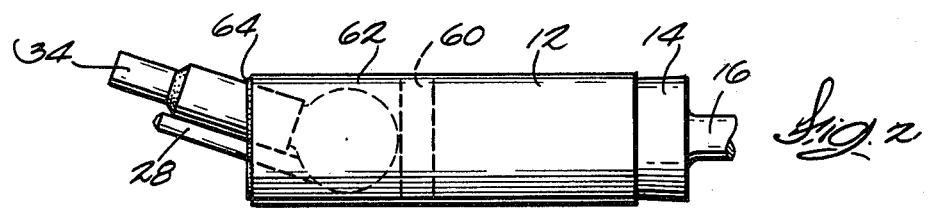
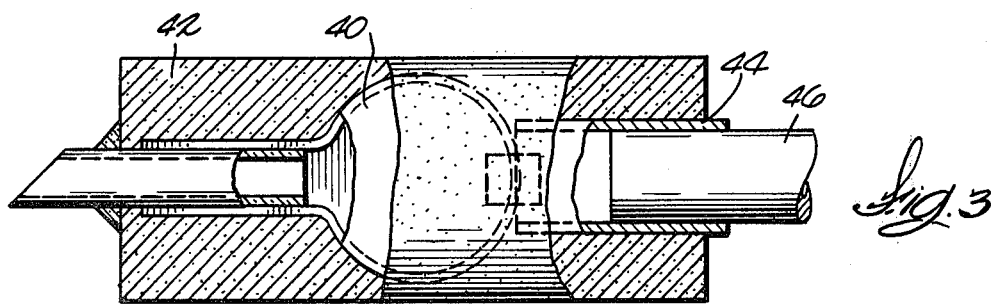
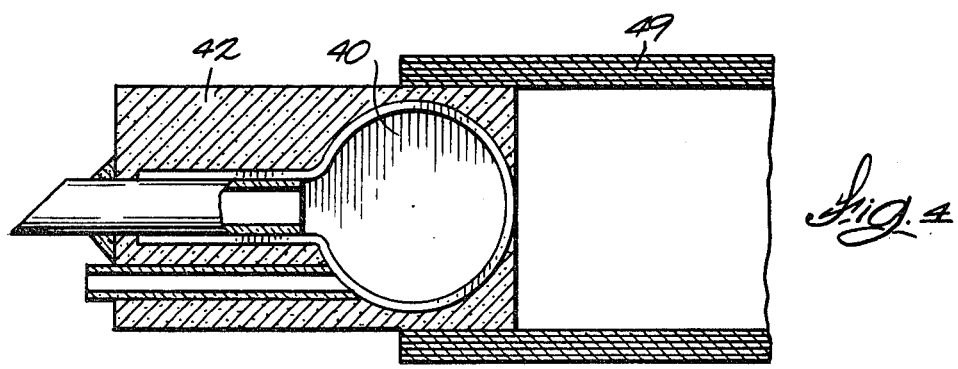

MOLDED SAND INSULATED SAMPLER

BACKGROUND OF THE INVENTION

My U.S. Pat. No. 3,791,219 discloses an immersion sampler in which metal mold halves are contained in a paperboard sleeve during the sampling procedure. A pin sample tube extends into the mold cavity for forming a pin sample. My U.S. Pat. No. 3,859,857 discloses various types of stream samplers for taking a sample from a flowing stream of molten metal as when metal is being poured into a ladle, etc. One of the objectives of every sampler is to facilitate retrieval of the sample from the mold halves as well as provide mold halves which are uniform and suitable for analysis. Controlling venting of molds, minimizing metal splash on the outside of the molds, good sample release and low cost are all desirable objectives.

SUMMARY OF THE INVENTION

The invention provides molten metal samplers which achieve these objectives. The mold halves are encased or cast in a sand-sodium silicate cement mix which seals the split line between the mold halves to prevent molten metal flow outwardly from the split line but does afford venting for good metal flow into the sample cavity. The sand-cement mix also enables easy release of the sample from the mold.

Further objects, advangtages and features of this invention will become apparent from the disclosure.

DESCRIPTION OF THE DRAWINGS

FIG. 1 is a fragmentary sectional view of a sampler in accordance with the invention.

FIG. 2 is a diagrammatic view of a modified embodiment of the invention.

FIG. 3 is a sectional view of a further modified embodiment of the invention.

FIG. 4 is a sectional view of a further modified embodiment of the invention.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

In the drawings, FIG. 1 shows a sampler 10 which includes a thin paperboard sleeve 12 adapted to receive a tapered plug 14 connected to a pipe 16 used for manipulation of the sampler. The sample mold 18 comprises two metal mold halves which can be similar in form to that disclosed in my U.S. Pat. No. 3,791,219. The metal mold halves have semi-cylindrical neck portions 20 which receive a fused quartz fill tube 22. In FIG. 1, the fill tube has a beveled end 24 to promote filling of the sample cavity 26. A pin sample tube 28 is also disclosed. As thus far described, the apparatus is disclosed in my prior patents.

The invention relates to the use of a sandsodium silicate cement mix 30 which is molded in place and with the sleeve 12 forming the mold. The sandsodium silicate mix isolates the metal mold halves from the wall of the paperboard tube. It has been found that because the sand has a relatively fixed and uniform porosity, the sand provides uniform venting of air around the split line between the mold halves which provides rapid and complete filling of the mold cavity 26. The sand, although it enables venting, seals the metal in the mold halves at all temperatures and pressures encountered in typical metal sampling. Moreover, the sand-cement mix protects the molds from a splash of molten metal from the outside during the filling operation. The sand is cheap and provides a slight chill to the sample and enables quick and easy release of the sample mold from the sand.

In FIG. 2, a sampler is disclosed in which the beveled end 24 is omitted and a tip 34 at 90° with the longitudinal axis of the fill tube is employed. The sand-cement mix is employed to position and maintain the fill tube at the desired angle.

FIG. 3 shows a modified embodiment in which the metal mold halves 40 are encased in the sand-cement mix 42 and a small cardboard sleeve 44 is also anchored in the cement at one end of the sample mold and provides a connection for manipulation by a pipe 46.

In FIG. 4, a further modified embodiment of the invention is disclosed in which the mold halves 40 are similarly encased with a mix 42 and a heavy paperboard sleeve 49 interfits on the periphery of the molded sand. The paperboard sleeve 49 is employed to manipulate the sampler.

Loose sand can be employed to fill or pack a cavity around mold parts and then a zone of sand-cement mix can be positioned to seal the loose sand in place. In FIG. 2, a zone 60 of sand-cement seals loose sand in the zone 62 between zone 60 and an end wall 64. The loose sand provides a closer fit or packing around the mold halves.

In addition to packing or casting sand around the samplers illustrated in my drawings, sand-casting can be employed with any of my samplers, such as those illustrated in my U.S. Pat. Nos. 4,069,717; 4,140,019; 3,805,621; 3,905,238; 4,010,649 and 4,116,070, the subject matter of which is incorporated herein by reference.

Any suitable sand and cement can be employed. Washed graded sand provides more uniform porosity for predictable venting characteristics. A sand that has provided good results is silica sand with 54 AFS fineness with less than 10% pass through 240 mesh screen. A suitable cement desirably cures at less than 200° F. or at room temperature.

I claim:

1. A molten metal sampler comprising a mold body defining a sample cavity, a sleeve around said sample cavity, including loose sand fill within said sleeve and surrounding said mold body, and a zone of sand-cement sealing said loose sand in place.

2. A method of making a molten metal sampler comprising the steps of providing an outer sleeve, inserting a mold body having a fill opening in the sleeve and packing the sleeve with a sand-sodium silicate mix to anchor said mold body in said sleeve.

* * * * *